United States Patent [19]

Gidda et al.

[11] Patent Number: 5,434,174

[45] Date of Patent: Jul. 18, 1995

[54] ISOXAZOLE DERIVATIVES FOR THE TREATMENT OF IRRITABLE BOWEL SYNDROME

[75] Inventors: Jaswant S. Gidda, Carmel; John M. Schaus, Zionsville, both of Ind.

[73] Assignee: Eli Lilly and Company, Indianapolis, Ind.

[21] Appl. No.: 49,968

[22] Filed: Apr. 20, 1993

Related U.S. Application Data

[63] Continuation of Ser. No. 916,281, Jul. 17, 1992, abandoned.

[51] Int. Cl.$^6$ ............................................. A61K 31/42
[52] U.S. Cl. ................................... 514/378; 514/379; 514/380
[58] Field of Search ........................ 514/378, 379, 380

[56] References Cited

U.S. PATENT DOCUMENTS 5,096,908  3/1992  Gidda et al. ...................... 514/307
5,158,956  10/1992  Gidda et al. ...................... 514/278

FOREIGN PATENT DOCUMENTS 0339982  11/1990  European Pat. Off. ... C07C 211/42
WO90/15047  12/1990  WIPO ........................ C07C 237/48
WO91/09853  7/1991  WIPO ........................ C07D 311/58

OTHER PUBLICATIONS

Talley, *Aliment. Pharmacol. Ther.*, 6(3), 273 (1992).
Bazzocchi, et al., *Curr. Ther. Res. Clin. Exp.*, 52(1), 135 (1992).
*Chem. Abst.*, 115(3), 28923v (1991).
*Chem. Abst.* 115(3), 28924w (1991).
C. J. Fowler, et al., *Life Sciences*, 48:959–967 (1990).
Gerald Friedman, MD. *Gastroenterology Clinics of North America*, 20:325–333 (1991).
Tonini et al., "5-Hydroxytryptamine$_4$ Receptor Agonists Facilitate Chloinergic Transmission . . . ", *Life Sciences*, vol. 50, (1992) pp. Ll–173–PL–178.

*Primary Examiner*—Raymond Henley, III
*Assistant Examiner*—M. Moezie
*Attorney, Agent, or Firm*—Douglas J. Taylor

[57] ABSTRACT

Methods of treating Irritable Bowel Syndrome (IBS) using a series of isoxazole derivatives that have both 5-HT1A agonist and M1 muscarinic activities, and formulations adapted for the treatment of IBS comprising those derivatives.

39 Claims, No Drawings

ISOXAZOLE DERIVATIVES FOR THE TREATMENT OF IRRITABLE BOWEL SYNDROME

This application is a continuation of application Ser. No. 07/916,281, filed on Jul. 17, 1992, now abandoned.

BACKGROUND OF THE INVENTION

Irritable Bowel Syndrome (IBS) is a motor disorder consisting of altered bowel habits, abdominal pain, and the absence of detectable pathology. IBS is recognized by its symptoms, which are markedly influenced by psychological factors and stressful life situations.

IBS is one of the most commonly encountered gastrointestinal disorders. Between 20% and 50% of patients referred to gastrointestinal clinics suffer from IBS. Symptoms of IBS occur in approximately 14% of otherwise apparently healthy people. It is one of the least understood disorders, in part because it is not a disease but a syndrome composed of a number of conditions with similar manifestations.

The major symptoms of IBS (altered bowel habits, abdominal pain and bloating) are manifestations of increased motility in the gut and hyper-secretion of gastric acid.

Activity of the GI tract is modulated neurally by the central nervous system (CNS) via parasympathetic and sympathetic innervation and by the peripherally located enteric nervous system (ENS) which resides within the GI tract itself.

The ENS is also very well organized and consists of all elements essential for coordinating the activity of the organ even in the absence of central input. See Goyal, R. K. "Neurology of the Gut", *Gastrointestinal Disorders*, Ed., Sleisenger and Fordtran, Saunders (1983), pp 97-114.

Serotonin (5-hydroxytryptamine, 5-HT) is associated directly or indirectly with a number of physiological phenomens, including appetite, anxiety and depression. R. A. Glennon *J. Med. Chem.* 30, 1 (1987). 5-HT receptors have been identified in the CNS and in peripheral tissues including the gastrointestinal tract, lung, heart, blood vessels, and various other smooth muscle tissues.

It has been recognized that there are multiple types of 5-HT receptors. These receptors have been classified as 5-HT1, 5-HT2, 5-HT3, and 5-HT4, with at least the 5-HT1 receptor being further divided into subclasses identified as 5-HT1A, 5-HT1B, 5-HT1C, and 5-HT1D.

In the CNS, 5-HT receptors are located post-synaptically, on neurons that receive sertonergic input, and presynaptically on 5-HT releasing neurons. The presynaptic receptors are believed to function to sense the concentration of 5-HT in the synaltic cleft and modulate the further release of 5-HT accordingly.

Generally, an "agonist" is a chemical compound that mimics the action of the endogenous neurotransmitter at receptors.

Direct-acting serotonin agonists are chemical substances that bind to and mimic the action of serotonin on serotonin receptors.

Indirect-acting serotonin agonists are chemical substances that increase the concentration of serotonin in the synaptic cleft. Indirect serotonin agonists include inhibitors of a serotonin specific uptake carrier, agents that release serotonin from storage granules, agents (serotonin precursors) that increase serotonin formation, and monoamine oxidase (MAO) inhibitors that block serotonin degradation and thereby increase the amount of serotonin available.

Serotonin is known to have a number of actions in the gastrointestinal tract. It is known that the intravenous infusion in humans of 5-HT or 5-HTP (5-hydroxytryptophane) inhibits the volume and acidity of both spontaneous and histamine-induced gastric secretion while simultaneously increasing the production of mucus. *Handbook of Experimental Pharmacology*, Vol. XIX, "5-Hydroxytryptamine and Related Indolealkylamines", Erspamer, V., sub-ed., Springer-Verlog, N.Y., 1966, pp. 329-335. It is not known whether binding at one or some combination of 5-HT receptor sites is required to effect this inhibition response or which receptor(s) are involved.

It is known that 5-HT receptors in smooth muscle of the gastrointestinal tract mediate contraction of this tissue. The rat fundus and guinea pig ileum are widely used for in vitro studies of 5-HT agonists and antagonists. The enterochromaffin cells of the gastrointestinal tract are the major sites of 5-HT production in the body.

Motility in the gut is also greatly influenced by cholinergic receptors. It is known that acetylcholine enhances gastrointestinal motility by acting at muscarinic receptors. However, at least five different muscarinic receptors (M1-M5) are known. See Barry B. Wolfe: In the Muscarinic Receptors. Ed. By J. H. Brown, *The Humana Press*, N.J. 1989, pp 125-150.) The relative role of these receptors in modulating gastrointestinal motility is not known because selective agonists and antagonists of these receptors have not been identified. In IBS compounds acting as muscarinic antagonists, such as Bentyl, are useful therapies but show serious side effects.

Current treatment for IBS is restricted to drugs which treat only a small proportion of patients. For example, anticholinergic drugs reduce spasticity, thereby relieving some of the abdominal pain. On the other hand, histamine $H_2$ receptor antagonists inhibit gastric acid secretion and, thus, may relieve dyspeptic symptoms. A therapeutic agent that relieves most of IBS symptoms is currently not available.

It has been discovered that 5HT1A agonists inhibit gastric acid secretion by acting directly on 5HT-receptor and, thus, may relieve dyspeptic symptoms. We have found a series of these agonist compounds that have also been shown to have affinity for M1-cholinergic receptors in binding studies and to have in vitro antispastic activity. Therefore, the compounds of this invention should be especially useful in the treatment of IBS.

This invention provides a group of compounds that are both direct acting 5-HT1A agonists and M1-cholinergic-receptor selective agents. Since these two characteristics are important to normalize the bowel habits and reduce the abdominal pain and distension of IBS, these agents which have this combination of activities should, therefore, act to normalize gastrointestinal motility and, be useful in the treatment of IBS conditions.

Other objects, features and advantages of the present invention will become apparent to one skilled in the art from the subsequent description and the appended claims.

SUMMARY OF THE INVENTION

This invention provides a method of treating Irritable Bowel Syndrome (IBS) in mammals comprising administering to a mammal in need of IBS treatment an effective dose of a compound of the formula I

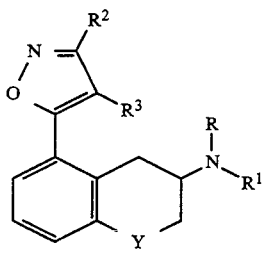

wherein:
R is hydrogen, $C_1$-$C_3$ alkyl, allyl, or

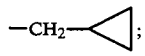

$R^1$ is hydrogen, $C_1$-$C_3$ alkyl, allyl,

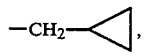

or —$(CH_2)_n$—X;
n is 1 to 5;
X is an optionally substituted phenyl, $C_1$-$C_3$ alkoxy, or $C_1$-$C_3$ alkylthio;
$R^2$ and $R^3$ are independently hydrogen, $C_1$-$C_3$ alkyl, $C_1$-$C_3$ alkoxy, $C_1$-$C_3$ alkylthio, halo, CN, or phenyl; or together are —$(CH_2)_p$—;
p is 3 to 6;
Y is —$CH_2$—, —O—, —$SO_m$—;
m is 0, 1, or 2;
or a pharmaceutically acceptable acid addition salt or solvate thereof.

Another embodiment of this invention is a pharmaceutical formulation adapted for the treatment of IBS comprising a compound of formula I and a pharmaceutically acceptable carrier, diluent or excipient therefor.

DETAILED DESCRIPTION OF THE INVENTION

The general chemical terms used in formula I have their usual meaning. For example, the term "alkyl" represents a straight or branched alkyl chain having the indicated number of carbons. $C_1$-$C_3$ alkyl groups are methyl, ethyl, n-propyl, and isopropyl;

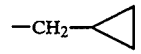

is cyclopropylmethyl.

Halo refers to bromine, chlorine, fluorine or iodine.

Optionally substituted phenyl means a phenyl ring which may contain one or two substituents from the following list: $C_1$-$C_3$ alkyl, $C_1$-$C_3$ alkoxy, $C_1$-$C_3$ alkylthio, halo, $NO_2$ and CN.

Irritable Bowel Syndrome is the most suitable and accurate term currently available for the disorder that can be treated by the methods of this invention. The term IBS emphasizes that the condition is a motor disorder manifesting irritability, that it is not a single disease but a syndrome, and that many areas of the gut are involved. Many of the other commonly used terms for the disorder, such as nervous, unstable, or spastic colon or colitis, are inadequate, inaccurate, or both.

An international working team report defines IBS as a functional gastrointestinal disorder manifested by (1) abdominal pain and/or (2) symptoms of disturbed defecation (urgency, straining, feeling of incomplete evacuation, altered stool form [consistency] and altered bowel frequency/timing) or (3) bloating (distention).

A recent revision proposes the criterion: abdominal pain or discomfort, relieved with defecation or associated with a change in frequency or consistency of stool, and three or more of the following: (1) altered stool frequency; (2) altered stool form (hard or loose/watery); (3) altered stool passage (straining or urgency, feeling of incomplete evacuation); (4) passage of mucus; and (5) bloating or a feeling of abdominal distention. Schuster, M. M., *Gastroenterology Clinics of Health America*, 20, 269–278 (1991).

Therefore, it will be understood that the compounds of this invention treat the Irritable Bowel Syndrome, however now or later defined, as manifested by its symptoms or cluster of symptoms.

The symptoms that help distinguish IBS from organic disease are (1) visible abdominal distension, (2) relief of abdominal pain by bowel movement, (3) more frequent bowel movements with the onset of pain, and (4) looser stools with onset of pain. Schuster, M. M., *Gastrointestinal Diseases*, Ed., Sleisenger and Fordtran, Saunders (1983), 880–895.

As mentioned hereinabove, useful compounds for practicing the method of the present invention include pharmaceutically acceptable acid addition salts of the compounds defined by the above formula I. Since these compounds are amines, they are basic in nature and accordingly react with any of a number of inorganic and organic acids to form pharmaceutically acceptable acid addition salts. Since the free amines of these compounds are typically oils at room temperature, it is preferable to convert the free amines to their corresponding pharmaceutically acceptable acid addition salts for ease of handling and administration, since the latter are routinely solid at room temperature. Acids commonly employed to form such salts are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenylsulfonic acid, carbonic acid, succinic acid, citric acid, benzoic acid, acetic acid, and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, hydrochloride, hydrobromide, hydroiodide, acetate, propionate, decanoate, caprylate, acrylate, formate, isobutyrate, caproate, heptanoate, propiolate, oxalate, malonate, succinate, suberate, sebacate, fumarate, maleate, 2-butyne-1,4-dioate, 3-hexyne-2,5-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, γ-hydroxybutyrate, glycollate, tartrate, methanesulfonate, propanesulfonate, naphthalene-1-sulfonate, naphthalene-2-sulfonate, mandelate, and the like. Preferred pharmaceutically acceptable acid addition salts are those formed with mineral acids such as hydrochloric acid and hydrobromic acid, and those formed with organic acids such as maleic acid.

In addition, some of these salts may form solvates with water or organic solvents such as ethanol. Such solvates also are included within the scope of this invention.

The compounds of the present invention are useful for treating IBS by virtue of their unique ability to modulate the function of both the 5-HT$_{1A}$ and muscarinic (M$_1$) receptors in mammals. Preferred classes of formula I are those wherein (a) R is C$_1$–C$_3$ alkyl or

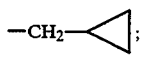

(b) R$^1$ is C$_1$–C$_3$ alkyl or

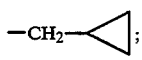

(c) R$^1$ is propyl;
(d) R$^2$ and R$^3$ are independently hydrogen or C$_1$–C$_3$ alkyl;
(e) R$^2$ and R$^3$ are together —(CH$_2$)$_p$;
(f) Y is O or —(CH$_2$)—.

Especially preferred are those formula I classes wherein
(a) R is propyl; and
(b) R$^2$ and R$^3$ are independently hydrogen or methyl.

Particularly preferred formula I compounds are:
(a)  8-(isoxazol-5-yl)-2-di-n-propylamino-1,2-3,4-tetrahydronaphthalene;
(b)  8-(4-methylisoxazol-5-yl)-2-dipropylamino-1,2,3,4-tetrahydronaphthalene; and
(c)  8-(3-methylisoxazole-5-yl)-2-dipropylamino-1,2,3,4-tetrahydronaphthalene.

It will be understood that the above classes may be combined to form additional preferred classes.

The compounds of the present invention possess an asymmetric carbon represented by the carbon atom labeled with an asterisk in the following formula:

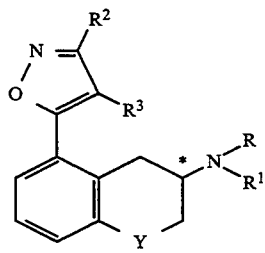

As such, each of the compounds exists as its individual d- and l-stereoisomers and also as the racemic mixture of such isomers. Accordingly, the compounds of the present invention include not only the dl-racemates but also their respective optically active d- and l-isomers.

The following compounds further illustrate compounds contemplated within the scope of this invention:
8-(isoxazol-5-yl)-2-(di-n-propylamino)tetrahydronaphthalene
8-(isoxazol-5-yl )-2-(propylamino)tetrahydronaphthalene
8-(isoxazol-5-yl)-2-(dimethylamino)tetrahydronaphthalene
8-(isoxazol-5-yl)-2-[di(cyclopropylmethyl)amino]tetrahydronaphthalene
8-(isoxazol-5-yl)-2-(di-allylamino)tetrahydronaphthalene
8-(3-methylisoxazol-5-yl)-2-(dipropylamino)tetrahydronaphthalene
8-(3-methylisoxazol-5-yl)-2-(propylamino)tetrahydronaphthalene
8-(3-methylisoxazol-5-yl)-2-(dimethylamino)tetrahydronaphthalene
8-(3-methylisoxazol-5-yl)-2-[di(cyclopropylmethyl)amino]tetrahydronaphthalene
8-(3-methylisoxazol-5-yl-2-(diallyl)amino)tetrahydronaphthalene
8-(4-methylisoxazol-5-yl)-2-(dipropylamino)tetrahydronaphthalene
8-(4-methylisoxazol-5-yl)-2-(propylamino)tetrahydronaphthalene
8-(4-methylisoxazol-5-yl)-2-(dimethylamino)tetrahydronaphthalene
8-(4-methylisoxazol-5-yl)-2-[di(cyclopropylmethyl)]aminotetrahydronaphthalene
8-(4-methylisoxazol-5-yl)-2-(diallylamino)tetrahydronaphthalene
8-(3,4-dimethylisoxazol-5-yl)-2-dipropylamino)tetrahydronaphthalene
8-(3,4-dimethylisoxazol-5-yl)-2-(propylamino)tetrahydronaphthalene
8-(3,4-dimethylisoxazol-5-yl)-2-(dimethylamino)tetrahydronaphthalene
8-(3,4-dimethylisoxazol-5-yl)-2-[di(cyclopropylmethyl)amino]tetrahydronaphthalene
8-(3,4-dimethylisoxazol-5-yl-2-(diallylamino)tetrahydronaphthalene
8-(4,5,6,7-tetrahydrobenz[c]isoxazol-1-yl)-2-(dipropylamino)tetrahydronaphthalene
8-(4,5,6,7-tetrahydrobenz[c]isoxazol-1-yl)-2-(propylamino)tetrahydronaphthalene
8-(4,5,6,7-tetrahydrobenz[c]isoxazol-1-yl)-2-(dimethylamino)tetrahydronaphthalene
8-(4,5,6,7-tetrahydrobenz[c]isoxazol-1-yl)-2-[di(cyclopropylmethyl)amino]tetrahydronaphthalene
5-(4,5,6,7-tetrahydrobenz[c]isoxazol-1-yl)-3-(dipropylamino)chromane
5-(isoxazol-5-yl)-3-(dipropylamino)chromane
5-(3-methylisoxazol-5-yl)-3-(dipropylamino)chromane
5-(4-methylisoxazol-5-yl)-3-(dipropylamino)chromane
5-(3,4-dimethylisoxazol-5-yl)-3-(dipropylamino)chromane
5-(isoxazol-5-yl)-3-(dipropylamino)thiochromane
5-(3-methylisoxazol-5-yl)-3-(dipropylamino)thiochromane
5-(4-methylisoxazol-5-yl)-3-(dipropylamino)thiochromane
5-(3,4-dimethylisoxazol-5-yl)-3-(dipropylamino)thiochromane The compounds of the present invention may be prepared by procedures well known to those of ordinary skill in the art. Those procedures are also fully described in co-pending U.S. application Ser. No. 07/653,583 filed on Feb. 8, 1991.

The compounds of this invention are available by a number of general reactions. General schemes are provided below; in each, the groups are as follows:

$R^2$, $R^3$: hydrogen, $C_1$–$C_3$ alkyl, halo, OH, $C_1$–$C_3$ alkoxy, $C_1$–$C_3$ alkylthio, $NH_2$, CN, phenyl, or (—$CH_2$—)$_p$;

$R_c$: hydrogen or $C_1$–$C_3$ alkyl;

X: halo, $SR_c$, $OR_c$, or $N(R_c)_2$.

Ar: the remaining portion of the formula I compound, i.e.,

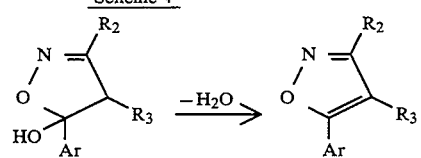

Scheme 1

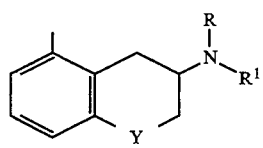

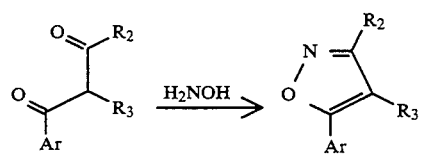

Scheme 2

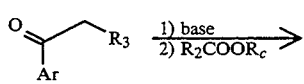

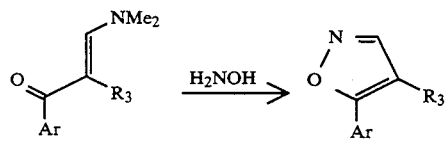

Scheme 3

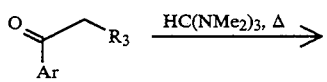

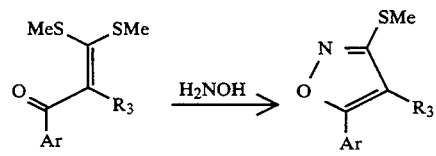

Scheme 4

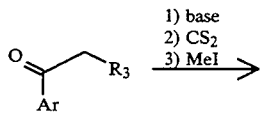

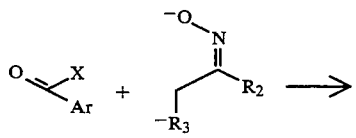

Scheme 4 -continued

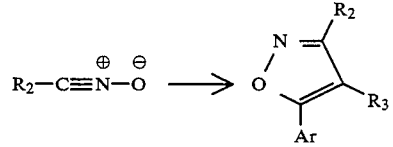

Scheme 5

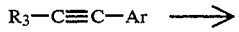

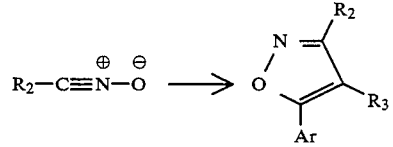

The aforementioned methods of synthesis provide compounds in which the heteroaromatic ring may or may not bear a substituent. General reactions providing methodology for incorporating, interconverting, and removing substituents on the heteroaromatic ring are cited in *Comprehensive Organic Transformations* by Richard C. Larocke, VCH Publishers, Inc., New York (1989).

The optically active isomers of the formula I compounds are also considered part of this invention. Such optically active isomers may be prepared from their respective optically active precursors by the procedures described above, or by resolving the racemic mixtures. These procedures are also described in co-pending U.S. application Ser. No. 07/653,583 filed on Feb. 8, 1991.

The compounds employed as initial starting materials in the synthesis of the compounds of this invention either are well known or can readily be synthesized by standard procedures commonly employed by those of ordinary skill in the art.

The pharmaceutically acceptable acid addition salts of this invention are typically formed by reacting a formula I base of this invention with an equimolar or excess amount of acid. The reactants are generally combined in a solvent in which they are soluble such as diethyl ether or benzene, and the salt normally precipitates out of solution within about one hour to 10 days, and can be isolated by filtration.

The following preparations are provided to describe typical methods for preparing the compounds of formula I. Other methods for their preparation will be apparent to those in the art. They are thus provided for purposes of illustration only and are not to be construed as limiting the scope of the instant invention in any way.

PREPARATION 1

Preparation of 2-(Di-n-propylamino)-8-(isoxazol-5-yl)-1,2,3,4-tetrahydronaphthalene maleate A solution of 2-(di-n-propylamino)-8-acetyl-1,2,3,4-tetrahydronaphthalene (0.3 g, 1.1 mmol), as prepared in co-pending U.S. application Ser. No. 07/653,583, and tris(dimethylamino)methane (0.32 g, 2.2 mmol) in toluene was heated to reflux for 5 hours and at 60° for 18 hours. An additional aliquot of tris (dimethylamino)methane (0.16 g, 1.1. mmol) was added and the reaction stirred at 60° for an additional 2 hours. The reaction was concentrated to give 2-(di-n-propylamino)-8-[1-oxo-3-(dimethylamino)-prop-2-en-1-yl]-1,2,3,4-tetrahydronaphthalene (0.39 g) as a viscous, orange oil.

Hydroxylamine hydrochloride (0.32 g, 4.6 mmol) was added to a solution of 2-(di-n-propylamino)-8-[1-oxo-3-(dimethylamino)-prop-2-en-1-yl]-1,2,3,4-tetrahydronaphthalene (0.75 g, 2.29 mmol) in acetic acid (5 ml) and the reaction stirred at room temperature. The reaction was concentrated and the residue dissolved in water. This solution was made basic by the addition of concentrated ammonium hydroxide solution and extracted with ether. The extract was washed with brine, dried with $Na_2SO_4$, and concentrated to give a viscous, light orange oil. The maleate salt was formed according to standard procedures. Crystallization from ethanol/ether gave the title compound as off-white crystals (0.24 g). mp 136°-138°. Recrystallization of this salt from ethanol gave colorless crystals (155 mg). m.p. 139°-141°

Analysis: Theory: C, 66.65; H, 7.29; N, 6.76; Found: C, 66.86; H, 7.33; N, 6.79.

PREPARATION 2

Preparation of 2-(Di-n-propylamino)-8-(3-bromoisoxazol-5-yl)-1,2,3,4-tetrahydronaphthalene maleate To a solution of 2-(Di-n-propylamino)-8-iodo-1,2,3,4-tetrahydronaphthalene (4.3 g, 12.1 mmol), as prepared in co-pending U.S. application Ser. No. 07/653,583 triethylamine (100 ml) was added copper(I) iodide (228 mg), bis(triphenylphosphine)-palladium(II) chloride (841 mg) and trimethylsilylacetylene (1.7 ml). This mixture was stirred at room temperature overnight. The reaction was poured into water and extracted with ether. The extract was washed with brine, dried ($Na_2SO_4$), and concentrated to give 5 g of crude product. Purification by flash chromatography using 20:1 methylene chloride:methanol as solvent gave 4.33 g of 2-(di-n-propylamino)-8-(2-trimethylsilylethynyl)-1,2,3,4-tetrahydronaphthalene which was used in the next reaction.

A solution of 2-(di-n-propylamino)-8-(2-trimethylsilylethynyl)-1,2,3,4-tetrahydronaphthalene (4.3 g) and tetraethylammonium fluoride (12.1 mmol) in tetrahydrofuran (150 ml) was stirred at room temperature for 18 hours and at reflux for 6 hours. The reaction mixture was concentrated and the residue dissolved in methylene chloride. This solution was washed with water, dried ($Na_2SO_4$), and concentrated to give 3.6 g of a brown oil. Purification by flash chromatography using 20:1 methylene chloride:methanol as solvent gave 2-(di-n-propylamino)-8-ethynyl-1,2,3,4-tetrahydronaphthalene (1.1 g, 36% overall yield).

2-(Di-n-propylamino)-8-ethynyl-1,2,3,4-tetrahydronaphthalene (900 mg; 3.5 mmol) was stirred at room temperature in 90 ml of ethyl acetate containing 1 ml of water. $Br_2CNOH$ (715.8 mg) in 10 ml of ethyl acetate was added, and the mixture was stirred at room temperature for two days after which 150 mg of potassium carbonate and 250 mg of $Br_2CNOH$ were added. The mixture was stirred for an additional four hours after which it was poured into water and washed with ethyl acetate. The ethyl acetate washes were combined, dried, and concentrated to obtain a residue of 1.0 g. The residue was purified by flash column chromatography using 20:1 $CH_2Cl_2$:MeOH. The appropriate fractions were combined to obtain about 120 mg of material. Ether was added and a solid was formed which was removed by filtration. The filtrate contained the desired product which was then converted to the maleate salt. Crystallization from a mixture of ethyl acetate and hexane gave the title compound (84 mg). m.p. 113°-114° C.

Analysis: Theory: C, 55.99; H, 5.92; N, 5.68; Found: C, 55.77; H, 5.90; N, 5.48.

PREPARATION 3

Preparation of 2-(Di-n-propylamino)-8-(4-methylisoxazol-5-yl)-1,2,3,4-tetrahydronaphthalene maleate 2-(Di-n-propylamino)-8-bromo-1,2,3,4-tetrahydronaphthalene (8.5 g.; 27.4 mmol) was dissolved in 80 ml of tetrahydrofuran (THF) and cooled to −78° C., after which 25.7 ml of n-butyllithium (1.6M in hexane) were added. The mixture was stirred at −78° C. for one hour after which 2.4 ml (32.9 mmol) of propionaldehyde were added. The mixture was warmed to room temperature and then poured into water, and extracted with methylene chloride. The extract was dried over sodium sulfate and evaporated to give 9.1 g of a yellow oil.

The oil was placed on a silica gel column and was eluted with a mixture of 3% methanol in methylene chloride containing a trace of ammonium hydroxide. The appropriate fractions were combined to give 6.5 g (82.0%) of 2-(di-n-propylamino)-8-(1-hydroxyprop-1-yl)-1,2,3,4-tetrahydronaphthalene as a clear oil.

The foregoing product was dissolved in 250 ml of methylene chloride, and 17.0 g (78.7 mmol) of pyridinium chlorochromate (PCC) were added along with 30 g 4A molecular sieves. The mixture was stirred for three hours at room temperature, after which 250 ml of ether and Celite were added. The mixture was poured onto a silica gel column and eluted with ether. Methanol was added to dissolve the brown sludge which had precipitated upon addition of ether to the reaction. This material was added to the column and eluted with 10% methanol in methylene chloride. The eluent was concentrated to give a brown oil which was further purified by silica gel column chromatography employing 2:1 hexanes:ether and then pure ether as solvent. Fractions containing the product were combined and concentrated to give 4.7 g of 2-(di-n-propylamino)-8-propionyl-1,2,3,4-tetrahydronaphthalene.

2-(Di-n-propylamino)-8-propionyl-1,2,3,4-tetrahydronaphthalene, (1.5 g; 5.2 mmol) was dissolved in 50 ml toluene, and 2.2 ml of tris(dimethylamino)methane was added. The mixture was heated to 80° C. overnight. The mixture was then evaporated and the residue was taken up in 15 ml of acetic acid. Hydroxylamine hydrochloride (730 mg; 10.4 mmol) was added, and the mixture was stirred at room temperature overnight. The mixture was poured onto water, the pH was adjusted to 11 with ammonium hydroxide, and the resulting mixture was extracted with methylene chloride. The extract was dried over sodium sulfate and evaporated to give 1.5 g of an orange oil.

The oil was placed on a silica gel column and was eluted with a 2:1 mixture of hexane and ether containing a trace of ammonium hydroxide. The appropriate fractions were combined to give 1.0 g (61.3%) of the free base of the title compound.

Fifty mg of the free base were converted to the maleate salt according to standard procedures and recrystallized from a mixture of ethanol and ether to give 55 mg of white crystals, m.p. 118° C.

Analysis, calcd. for $C_{24}H_{32}N_2O_5$: Theory: C, 67.27; H, 7.53; N, 6.54; Found: C, 66.99; H, 7.60; N, 6.35.

PREPARATION 4

Preparation of 2-(Di-n-propylamino)-8-(4-ethylisoxazol-5-yl)-1,2,3,4-tetrahydronaphthalene 2-(Di-n-propylamino)-8-bromo-1,2,3,4-tetrahydronaphthalene (5.0 g; 16.1 mmol) was dissolved in 50 ml of THF, and the mixture was cooled to −78° C. after which 21.0 ml of n-butyllithium (0.92M in hexane) were added. The mixture was stirred for 30 minutes, and 1.85 ml (21.0 mmol) of butyraldehyde were added. The mixture was allowed to warm to room temperature and was stirred overnight, after which it was poured into water and extracted with methylene chloride. The extract was dried over sodium sulfate and evaporated to give 6.4 g of a residue. The residue was placed on a silica gel column and was eluted with a mixture of 2% methanol in methylene chloride containing a trace of ammonium hydroxide. The appropriate fractions were combined to give 4.8 g of 2-(di-n-propylamino)-8-(1-hydroxybut-1-yl)-1,2,3,4-tetrahydronaphthalene as a thick oil.

The oil (4.0 g; 13.2 mmol) was dissolved in 200 ml of methylene chloride and 4A molecular sieves (30 g) were added. The mixture was stirred, and 10.0 g (46.2 mmol) PCC were added. Stirring was continued for three hours at room temperature, after which the mixture was poured onto a pad of silica gel and eluted sequentially with ether and 3% methanol in methylene chloride containing a trace of ammonium hydroxide to recover the product as a brown oil.

The oil was placed on a silica gel column and was eluted with a mixture of 3% methanol and methylene chloride containing a trace of ammonium hydroxide. The appropriate fractions were combined to obtain an oil which, when dissolved in ether, caused a brown precipitate to form. The precipitate was removed by filtration, and the filtrate was evaporated to give 3.0 g of 2-(di-n-propylamino)-8-butyryl-1,2,3,4-tetrahydronaphthalene as a light brown oil.

Potassium t-butoxide (0.82 g; 7.3 mmol) was suspended in 100 ml of tetrahydrofuran (THF). Ethyl formate (1.0 g; 13.3 mmool) and 2-(Di-n-propylamino)-8-butyryl-1,2,3,4-tetrahydronaphthalene (1.0 g; 3.3 mmol) in THF were added to the mixture. The resulting mixture was stirred at room temperature overnight. Hydroxylamine (1.2 g; 16.6 mmol) was added followed by sufficient water to dissolve the solid. The resulting mixture, having pH 6, was stirred at room temperature for 20 hours after which it was poured into water, and the pH was adjusted to 12 with ammonium hydroxide. The mixture was then extracted with methylene chloride. The extract was dried over sodium sulfate and evaporated. The residue was dissolved in 100 mg of toluene, and 100 mg of p-toluenesulfonic acid was added. The mixture then was refluxed for 1.5 hours after which it was poured into water and extracted with methylene chloride. The methylene chloride extract was dried over sodium sulfate and evaporated.

The residue was placed on a silica gel column and was eluted with a 2:1 mixture of hexane:ether containing a trace of ammonium hydroxide. The appropriate fractions were combined to give 0.9 g of the title compound. MS (FD): 327(100).

PREPARATION 5

Preparation of 2-(Di-n-propylamino)-8-(3-methylisoxazol-5-yl)-1,2,3,4-tetrahydronaphthalene maleate Potassium t-butoxide (450 mg; 4.0 mmol) was suspended in THF, and 0.7 ml (7.3 mmol) of ethyl acetate and 0.5 g (1.8 mmol) of 2-(di-n-propylamino)-8-acetyl-1-2,3,4-tetrahydronaphthalene in THF were added. The total amount of THF which was used was 30 ml. The mixture was then stirred overnight at room temperature after which 640 mg (9.2 mmol) of hydroxylamine hydrochloride were added. The reaction mixture was then stirred at room temperature for 64 hours. The mixture was poured into water and the pH was adjusted from 6 to 12 with ammonium hydroxide. The mixture then was extracted with a 3:1 mixture of chloroform: isopropyl alcohol. The extract was dried over sodium sulfate and evaporated to give 450 mg of a solid. The solid was dissolved in toluene; a small amount of p-toluenesulfonic acid was added; and the mixture was refluxed for two hours. The mixture then was poured into water; the pH was adjusted to 12 with ammonium hydroxide; and the mixture was extracted with methylene chloride. The methylene chloride extract was dried over sodium sulfate and evaporated to give 390 mg of a brown oil.

The oil was placed on a silica column and eluted with methylene chloride containing 2% methanol and a trace of ammonium hydroxide. The appropriate fractions were combined to give 210 mg (35%) of the free base of the title compound.

According to standard procedures, the compound was converted to the maleate salt which was recrystalized from a mixture of ethanol and ether to give 200 mg of the title compound, m.p. 125.5°–127.5° C. MS(FD): 313(100).

Analysis, calcd. for $C_{24}H_{31}N_2O_5$: Theory: C, 67.27; H, 7.53; N, 6.54; Found: C, 67.52; H, 7.29; N, 6.48.

PREPARATION 6

Preparation of 2-(Di-n-propylamino)-8-(3-phenylisoxazol-5-yl)-1,2,3,4-tetrahydronaphthalene hydrobromide Acetophenone oxime (750 mg; 5.5 mmol) was dissolved in THF, and the mixture was cooled to −5° C. n-Butyllithium (12.0 ml; 11.1 mmol) was added, and the mixture was stirred at −5° C. for one hour. 2-(Di-n-propylamino)-8-methoxycarbonyl-1,2,3,4-tetrahydronaphthalene (0.8 g; 2.8 mmol) dissolved in THF was added (total THF in the mixture equals 100 ml), and the mixture was warmed to room temperature. The mixture was then poured into water and extracted with methylene chloride. The extract was dried over sodium sulfate, and evaporated to give 1.4 g of a residue.

The residue was placed on a silica gel column and was eluted with a 2:1 mixture of hexane:ether containing a trace of ammonium hydroxide. The appropriate fractions were combined to give 220 mg of the free base of the title compound.

According to standard procedures, the free base was converted to the hydrobromide salt which was recrystallized from a mixture of methanol and ethyl acetate to give 150 mg of a white powder, m.p. 171.5°–173° C. MS(FD): 374(100) Analysis, calcd. for $C_{25}H_{30}N_2OBr$: Theory: C, 65.93; H, 6.86; N, 6.15; Found: C, 65.74; H, 6.86; N, 5.92.

PREPARATION 7

Preparation of
2-(Di-n-propylamino)-8-(3-methylthioisoxazol-5-yl)-
1,2,3,4-tetrahydronaphthalene maleate 2-(Di-n-propylamino)-8-[3,3-di(methylthio)-1-oxo-prop-2-en-1-yl]-1,2,3,4-tetrahydronaphthalene (0.64 g; 1.7 mmol), prepared as described in co-pending U.S. application Ser. No. 07/653,583, was dissolved in a mixture of toluene and acetic acid. Hydroxylamine hydrochloride (1.2 g; 17 mmol) and sodium acetate (1.2 g; 14 mmol) in 10 ml of water were added. Ethanol (10 ml) then was added to render the mixture homogeneous. The mixture was heated to 100° C. for 18 hours after which 0.6 g of hydroxylamine hydrochloride was added. The mixture was stirred at 100° C. for an additional four hours, and another 0.6 g of hydroxylamine hydrochloride was added. The mixture then was stirred for two hours at 100° C. and then at room temperature overnight. The mixture was poured into water, and the aqueous mixture was washed twice with ether and then extracted with 10% hydrochloric acid. The aqueous layers were combined and made basic (pH 12). The mixture was then extracted with methylene chloride, and the extract was dried over sodium sulfate and evaporated to give 560 mg of a dark yellow oil.

The oil was placed on a silica gel column and was eluted with a gradient of 1.5–2% methanol in methylene chloride containing a trace of ammonium hydroxide. The appropriate fractions were combined to give 230 mg of product. The product was converted to the maleate salt and recrystallized from a mixture of ethyl acetate and hexane to give 210 mg of the title compound, m.p. 118°–119.5° C. MS(FD): 344(100).

Analysis: Theory: C, 62.59; H, 7.00; N, 6.08; Found: C, 62.84; H, 7.04; N, 6.02.

PREPARATION 8

Preparation of
2-(Di-n-propylamino)-8-(4-methoxyisoxazol-5-yl)-
1,2,3,4-tetrahydronaphthalene hydrobromide 2-(Di-n-propylamino)-8-bromo-1,2,3,4-tetrahydronaphthalene (5.0 g; 16.1 mmole) was dissolved in 25 ml of THF and cooled to −78° C. after which 3.22 ml of n-butyllithium (1M in hexane) was added. The mixture was maintained at −78° C. for 1.5 hours. This solution was transferred via cannula to a solution of methyl methoxyacetate (7.5 ml, 160 mmol) in THF at −78° C. The reaction mixture was stirred at room temperature overnight, poured into NaHCO$_3$ solution and extracted with CH$_2$Cl$_2$. The extract was dried (Na$_2$SO$_4$) and concentrated to give 6.8 g of crude product.

The material then was chromatographed on silica gel, and the product was eluted using 4% methanol in methylene chloride containing a trace of ammonium hydroxide. The appropriate fractions were combined to give 1.4 g of 2-(di-n-propylamino)-8-methoxyacetyl-1,2,3,4-tetrahydronaphthalene.

A solution of 2-(di-n-propylamino)-8-methoxyacetyl-1,2,3,4-tetrahydronaphthalene (1.0 g) and tris(dimethylamino)methane (1.5 ml) in toluene (25 ml) was heated to reflux for 1.5 hours. The reaction was concentrated to give crude 2-(di-n-propylamino)-8-(1-oxo-2-methoxy-3-(dimethylamino)-prop-2-enyl)-1,2,3,4-tetrahydronaphthalene (1.2 g).

Hydroxylamine hydrochloride (1.2 g) was added to a solution of 2-(di-n-propylamino)-8-(1-oxo-2-methoxy-3-(dimethylamino)-prop-2-enyl)-1,2,3,4-tetrahydronaphthalene (1.1 g) in methanol and the reaction stirred at room temperature overnight. The reaction was concentrated and the residue dissolved in toluene. p-Toluenesulfonic acid (660 mg) was added to the solution and the reaction heated to reflux for 2 hours. The reaction was concentrated and the residue dissolved in a mixture of water and methylene chloride. This mixture was poured into a sodium bicarbonate solution, and the resulting mixture was extracted with methylene chloride. The extract was dried with MgSO$_4$ and concentrated to give an oil (600 mg). Purification by flash chromatography using 1:1 ether:hexanes as solvent provided 160 mg of the free base of the title compound. The hydrobromide salt was formed. Two recrystallizations from methanol/ether gave the title compound hydrobromide as white crystals (86 mg). m.p. 178° C.

Analysis: Theory: C, 58.68; H, 7.14; N, 6.84; Found: C, 58.88; H, 7.23; N, 6.60.

PREPARATION 9

Preparation of
S-(−)-8-(isoxazol-5-yl)-2-dipropylamino-1,2,3,4-tetrahydronaphthalene maleate A solution of S-(−)-8-acetyl-2-dipropyl-1,2,3,4-tetrahydronaphthalene maleate (5.0 g, 18.3 mmol), prepared as described in EP 0 399 982 A1, and tris(dimethylamino)methane (7.6 ml, 45.8 mmol) in toluene (200 ml) was heated to 80° for 20 hr. The solvent was removed and the residue dissolved in acetic acid (50 ml). Hydroxylamine hydrochloride (2.5 g, 36.6 mmol) was added and the reaction stirred at room temperature for 20 hr. The reaction was poured into water. The resulting mixture was made basic with NaOH solution and extracted with methylene chloride. The extract was dried (Na$_2$SO$_4$) and concentrated to give a dark red oil. Purification by flash chromatography (1:2, ether:hexanes (NH$_4$OH)) gave 4.3 g (79%) of the desired product. The salt was formed with maleic acid and crystallized from ethanol/ether to give light yellow crystals (5.3 g, mp 127°–128.5°). MS (FD): 298(100)

OR: $[\alpha]_D = 33.04°$ (c=1.0, H$_2$O); $[\alpha]_{365} = -57.34°$ (c=1.0, H$_2$O).

Analysis: calc. for C$_{19}$H$_{26}$N$_2$O.C$_4$H$_4$O$_4$.0.2 H$_2$O: Theory: C, 66.07; M, 7.33; N, 6.70; Found: C, 65.95; H, 6.92; N, 7.08.

PREPARATION 10

Preparation of
R-(+)-8-(isoxazol-5-yl)-2-dipropylamino-1,2,3,4-tetrahydronaphthalene maleate A solution of R-(+)-8-acetyl-2-dipropyl-1,2,3,4-tetrahydronaphthalene maleate (5.0 g, 18.3 mmol), as described in EP 0 399 982 A1, and tris(dimethylamino)methane (7.6 mL, 45.8 mmol) in toluene (200 mL) was heated to 80° for 20 hr. The solvent was removed and the residue dissolved in acetic acid (25 mL). Hydroxylamine hydrochloride (2.5 g, 36.6 mmol) was added, and the reaction mixture was stirred at room temperature for 20 hr. The reaction was poured into water and washed with ether. The resulting aqueous layer was made basic with NaOH solution and extracted with methylene chloride. The extract was dried (Na$_2$SO$_4$) and concentrated to give 5.1 g of crude product. Purification by flash chromatography (1:2, ether:hexanes (NH$_4$OH)) gave 4.6 g (83%) of the desired base. The salt was formed with maleic acid and crystallized from ethanol/ether to give a white solid (5.4 g, mp 127°–128.5°). MS (FD): 298(100)

Analysis, calcd. for $C_{19}H_{26}N_2O \cdot C_4H_4O_4 \cdot 0.2\ H_2O$: Theory: C, 66.07; H, 7.33; N, 6.70; Found: C, 65.71; H, 6.93; N, 7.14.

PREPARATION 11
Preparation of
R-(+)-8-(4-methyl-5-isoxazolyl)-2-(dipropylamino)-1,2,3,4-tetrahydronaphthalene hydrobromide A solution of R-(+)-8-propionyl-2-dipropylamino-1,2,3,4-tetrahydronaphthalene (2.0 g, 7.0 mmol) and tris(dimethylamino)methane (2.54 g, 2.9 mL, 17.4 mmol) in toluene (65 mL) was heated to reflux for 3 hr. The solvent was removed and the residue dissolved in acetic acid (20 mL). Hydroxylamine hydrochloride (0.97 g, 14 mmol) was added and the reaction stirred at room temperature for 3 days. The reaction was poured into water. The resulting mixture was made basic with NaOH solution and extracted with a 1:3 mixture of isopropanol and chloroform. The extract was dried ($Na_2SO_4$) and concentrated to give a yellow/orange oil. Purification by flash chromatography (1:1, ether:hexanes ($NH_4OH$)) gave 1.46 g (67%) of a colorless oil. The hydrobromide salt was formed and crystallized twice from THF/hexanes to give white crystals (1.32 g, mp 167°–169°).

OR: $[\alpha]_D = +27.26°$ (c=1.0, $H_2O$); $[\alpha]_{365} = +40.90°$ (c=1.0, $H_2O$).

Analysis: calcd for $C_{20}H_{28}N_2O \cdot HBr$: Theory: C, 61.07; H, 7.43; N, 7.12; Found: C, 61.21; H, 7.50; N, 6.97.

PREPARATION 12
Preparation of
5-(5-isoxazolyl)-3-(dipropylamino)chromane hydrobromide A solution of 5-acetyl-3-dipropylaminochromane (500 mg, 1.81 mmol), prepared as described in Patent Cooperation Treaty (PCT) No. WO 91/09853, and tris[dimethylamino]methane (540 mg, 5.4 mmol) in toluene (20 mL) was heated to reflux for 2 hr. TLC showed the presence of a new, lower Rf product. The reaction was diluted with dilute NaOH solution and extracted with a 1:3 mixture of isopropanol and chloroform. The extract was dried ($Na_2SO_4$) and concentrated to give a dark yellow oil. This material was dissolved in acetic acid (10 mL) and solid hydroxylamine hydrochloride (480 mg, 6.9 mmol) added. The reaction was stirred at room temperature for 17 hr, diluted with water, made basic with NaOH, and extracted with a 1:3 mixture of isopropanol and chloroform. The extract was dried ($Na_2SO_4$) and concentrated to give 534 mg of an orange oil. Purification by flash chromatography (1:1, ether:hexanes ($NH_4OH$)) gave the product as a colorless oil (482 mg, 88%). This material was converted to its hydrobromide salt and crystallized from ethyl acetate/hexanes to give a white solid. mp 171.5°–173°. MS (FD): 300 (100)

Analysis: calcd. for $C_{18}H_{24}N_2O_2 \cdot HBr$: Theory: C, 56.70; H, 6.61; N, 7.35; Found: C, 56.71; H, 6.56; N, 7.54.

As noted above, the compounds of this invention have binding affinity for both 5-HT1A and muscarinic ($M_1$) receptors.

The following experiments were conducted to demonstrate the ability of compounds of the present invention to bind to 5-HT1A receptors. Sites specifically labeled by tritiated 8-hydroxy-2-dipropylamino-1,2,3,4-tetrahydronaphthalene ($^3$H-8-OH-DPAT) have been identified as 5-HT1A receptors. This general procedure is set forth in Wong et al., J. Neural Transm. 71: 207–218 (1988).

In vitro Binding Methods to 5HT1A Receptors

Male Sprague-Dawley rats (110–150 g) from Harlan Industries (Cumberland, Ind.) were fed Purina Chow ad libitum for at least 3 days before being used in the studies. Rats were killed by decapitation. The brains were rapidly removed, and the cerebral cortices were dissected out at 4° C.

Brain tissues were homogenized in 0.32M sucrose. After centrifugation at 1000× g for 10 min. and then at 17000× g for 20 min., a crude synaptosomal fraction was sedimented. The pellet was suspended in 100 vol. of 50 mM Tris-HCl, pH 7.4, incubated at 37° C. for 10 min., and centrifuged at 50000× g for 10 min. The process was repeated and the final pellet was suspended in ice-chilled 50 mM Tris-HCl, pH 7.4.

Binding of $^3$H-8-OH-DPAT was performed according to the previously described method [Wong et al., J. Neural Transm. 64: 251–269 (1985)]. Briefly, synaptosomal membranes isolated from cerebral cortex were incubated at 37° C. for 10 min. in 2 ml of 50 mM Tris-HCl, pH 7.4; 10 mM pargyline; 0.6 mM ascorbic acid; 5 mM $CaCl_2$; 2 nM 3H-8-OH-DPAT and 0.1 to 1000 nm of the compound of interest. Binding was terminated by filtering samples under reduced pressure through glass fiber (GFB) filters. The filters were washed twice with 5 ml of ice cold buffer and placed in scintillation vials with 10 ml of PCS (Amersham/Searle) scintillation fluid. Radioactivity was measured with a liquid scintillation spectrometer. Unlabeled 8-OH-DPAT at 10 mM was also included in separate samples to establish non-specific binding. Specific binding of $^3$H-8-OH-DPAT is defined as the difference of radioactivity bound in the absence and in the presence of 10 μM unlabeled 8-OH-DPAT. The results are reported in Tables I and II.

In vivo Methods to Show 5HT1A Activity

Compounds of this invention were also examined for their in vivo effects on brain 5-HIAA and serum corticosterone levels. Male Sprague-Dawley rats weighing 150–200 g were administered subcutaneously or orally with aqueous solutions of the test compound. One hour after treatment, the rats were decapitated and trunk blood collected. The blood was allowed to clot and then was centrifuged to separate the serum. The concentration of corticosterone in the serum was determined by the spectrofluorometric method of Solem, J. H.; Brinck-Johnsen, T., Scand. J. Clin. Invest, [Suppl. 80], 17, 1 (1965). The whole brains from the decapitated rats were quickly removed, frozen on dry ice, and stored at −15° C. 5-HIAA concentrations were measured by liquid chromatography with electrochemical detection as described by Fuller, R. W.; Snoddy, H. D.; Perry, K. W., Life Sci. 40, 1921 (1987). The results are reported in Table I.

In vitro Binding Methods for [3H]-pirenzepine Binding

For in vitro 3H-pirenzepine binding, male Sprague-Dawley (Harlan Sprague Dawley, Indianapolis, Ind.) rats weighing 100–150 gm were sacrificed by decapitation, the brains were quickly removed, and the cerebral cortex was dissected from the brain. Cerebral cortical membranes were prepared by differential centrifugation, washed twice and frozen until used.

The inhibition of binding of 3H-pirenzepine to receptors was determined by adding study drug, 1 nM 3H-pirenzepine (87.0 Ci/mmol, New England Nuclear, Boston, Mass.), and about 100 ug cerebral cortical membranes in 1 ml total volume of 20 mM tris-Cl buffer, pH 7.4, containing 1 mM $MnCl_2$. After incubation for 1 hour at 25° C., the homogenates were filtered through glass filters (Whatman, GF/c) with vacuum, the filters were washed 3 times with 2 ml cold buffer, and placed in scintillation vials containing 10 ml scintillation fluid (Ready Protein +, Beckman, Fullerton, Calif.).

Radioactivity trapped on the filters was determined by liquid, scintillation spectrometry. Nonspecific binding was determined using 1 uM atropine.

The results are reported in Table II.

Gastric Acid Inhibition

Gastric acid inhibition was determined in pylorus ligated rats following the procedure by Shay (Shay, H., Komarov, A. A. and Greenstein, M: Effects of vagotomy in the rat, *Arch. Surg.* 59: 210–226, 1949). Male Sprague-Dawley rats weighing approximately 200 gm were starved 24 hours prior to using. Water was provided ad libitrim. Under light ether anesthesia the pylorus was ligated and simultaneously the rats were dosed with the compound either i.p. or s.c. and the rats were allowed to recover from anesthetic. Acid was accumulated for 2 hours. At the end of this period, rats were killed. Stomach contents were removed, measured and titrated to a pH endpoint of 7.0. Each experiment had a vehicle-treated control group for determining percent inhibition of secretion.

The results are reported in Table I.

Reversal of Carbachol-Induced Hypertone

Male Sprague-Dawley rats weighing 300–350 gm were starved for 24 hours. The rats were brought to the lab and decapitated and colons were removed immediately. Fecal content was washed and longitudinal strips 4 cm long were placed in organ baths under 1 gm tension using Grass FT03 transducers. Tissues were allowed to equilibrate and were gassed with 95% oxygen and 5% carbon dioxide. The tissues were then contracted with carbachol to produce a tonic response. Then the drug solutions were added to see relaxation. Percent relaxation was calculated from the pre-treatment control period. For many compounds more than one concentration of the drug was tested. In these situations an $IC_{50}$ was calculated, which is the dose which inhibited carbachol induced response by 50%. The results are reported in Table II.

Tables I and II, set forth below, show the results of the evaluation of various compounds of the present invention.

In Table I, the first column provides the preparation number of the compound evaluated; columns 2 and 3 show the substituted groups of $R^2$ and $R^3$; the fourth column provides the $IC_{50}$ value, expressed in nanomolar concentration, required to inhibit the binding of 3H-8-OH-DPAT to 5HT1A receptors; Column 5 shows % gastric acid inhibition at a dose or $ED_{50}$ value in µMoles/kg in vivo, column 6 provides the minimum effective dose (MED) of the test compound administered subcutaneously in lowering brain 5-HIAA levels; the seventh column provides the MED of the test compound administered subcutaneously in elevating serum corticosterone levels; the eighth column provides the same information as the sixth column except that the test compound is administered orally. The results in columns 6–8 are indicative of 5-HT1A agonist activity.

Table II summarizes the effect of typical formula I compounds on muscarinic ($M_1$) receptors. The first three columns are the same as in Table I. Column 4 describes $IC_{50}$ value, expressed in nanomolar concentration, required to inhibit the binding of 3H-pirenzepine to muscarinic ($M_1$) receptors; Column 5 shows the $IC_{50}$ values in µM to inhibit Carbachol induced hypertone in colonic smooth muscle in vitro.

TABLE I

5-HT1A Agonist Activity of Formula I Compounds

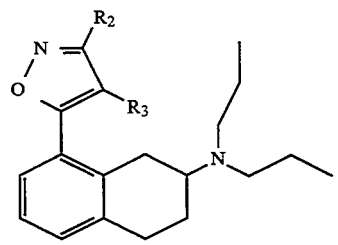

| Example No. | $R_2$ | $R_3$ | Radioligand binding data ($IC_{50}$, nM) 5-$HT_{1a}$ % | Gastric Acid Inhibition @ 10µ/moles | 5-HIAA MED (mg/kg. sc) | Corticosterone MED (mg/kg. sc) | 5-HIAA MED (mg/kg. po) |
|---|---|---|---|---|---|---|---|
| 8-OH DPAT (Std) | | | | 72.4 | | | |
| 1 | H | H | 0.44 | 69.6 | 0.1 | 0.3 | 3 |
| 9 | H | H | 0.2 | 96.8 | | | 3 |
| 10 | H | H | 1.4 | 47.1 | | | 10 |
| 2 | Br | H | 2.5 | | >1.0 | >1.0 | |
| 3 | H | $CH_3$ | 1.9 | 95.7 | 0.3 | 1.0 | >10 |
| 4 | H | Et | | | | | |
| 5 | $CH_3$ | H | 1.3 | 95.8 | 1.0 | >1.0 | |
| 6 | Ph | H | 72 | | | | |
| 7 | SMe | H | 1.2 | 65.4 | >1.0 | >1.0 | |
| 8 | H | OMe | 1.7 | 46.8 | 1.0 | >1.0 | |

TABLE II

Muscarinic ($M_1$) Activity of Formula I Compounds

| Example No. | $R_2$ | $R_3$ | Radioligand binding data ($IC_{50}$, nM) $M_1$ | Blockade of carbachol-induced contraction of rat colon (% Inhibition @ 10 μM/kg or $IC_{50}$) |
|---|---|---|---|---|
| 8-OH DPAT (Std) | | | 1940 | 29.75 |
| 1 | H | H | | 8.1 |
| 9 | H | H | 180 | 2.5 |
| 10 | H | H | 150 | 9.1 |
| 2 | Br | H | 220 | 4.6 |
| 3 | H | $CH_3$ | 190 | 58 @ 10 |
| 4 | H | Et | | |
| 5 | $CH_3$ | H | 107 | 65 @ 10 |
| 6 | Ph | H | 750 | |
| 7 | SMe | H | 173 | 67 @ 10 |
| 8 | H | OMe | 195 | 69 @ 10 |

Thus, one embodiment of the present invention is a method of treating Irritable Bowel Syndrome via modulating the activity of both the 5-HT1A and muscarinic ($M_1$) receptors which comprises administering to a mammal in need of treatment for IBS a pharmaceutically effective amount of a compound of formula I.

The term "pharmaceutically effective amount", as used herein, represents an amount of a compound of the invention which is capable of binding to both serotonin 1A and $M_1$ receptors. The specific dose of compound administered according to this invention will, of course, be determined by the particular circumstances surrounding the case, including, for example, the compound administered, the route of administration, and the condition being treated. A typical daily dose generally will contain from about 0.01 mg/kg to about 20 mg/kg of the active compound of this invention. Preferred daily doses generally will be from about 0.05 to about 10 mg/kg, and ideally from about 0.1 to about 5 mg/kg.

The compounds can be administered by a variety of routes including oral, rectal, transdermal, subcutaneous, intravenous, intramuscular, and intranasal.

The compounds of this invention are preferably formulated prior to administration. Therefore, another embodiment of the present invention is a pharmaceutical formulation comprising a compound of formula I and a pharmaceutically acceptable carrier, diluent or excipient therefor.

The present pharmaceutical formulations can be prepared by known procedures using well known and readily available ingredients. In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semisolid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, sterile packaged powders, and the like.

Examples of suitable carriers, excipients, and diluents are lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methylhydroxybenzoates, propylhydroxybenzoates, talc, magnesium stearate, and mineral oil. The formulations may additionally include lubricating agents, wetting agents, emulsifying agents, suspending agents, preserving agents, sweetening agents, flavoring agents, and the like. The compositions of the invention may be formulated so as to provide quick, sustained or delayed release of the active ingredient after administration to the patient by employing procedures known in the art.

The compositions are preferably formulated in a unit dosage form, each dosage generally containing from about 0.1 to about 500 mg, and preferably from about 1 to about 250 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

The following formulation examples are illustrative only and are not intended to limit the scope of the invention in any way.

FORMULATION 1

Hard gelatin capsules are prepared using the following ingredients:

| | Quantity (mg/capsule) |
|---|---|
| 2-(Di-n-propylamino)-8-(isoxazol-5-yl)-1,2,3,4-tetrahydronaphthalene hydrochloride | 250 |
| Starch, dried | 200 |
| Magnesium stearate | 10 |
| Total | 460 mg |

The above ingredients are mixed and filled into hard gelatin capsules in 460 mg quantities.

FORMULATION 2

A tablet is prepared using the ingredients below:

| | Quantity (mg/capsule) |
|---|---|
| 2-(Di-n-propylamino)-8-(4-methyl-isoxazol-5-yl)-1,2,3,4-tetrahydronaphthalene hydrochloride | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

FORMULATION 3

Suspensions, each containing 50 mg of active ingredient per 5 ml dose, are made as follows:

|  | Quantity (mg/capsule) |
|---|---|
| 2-Diallylamino-8-(3-phenylisoxazole-5-yl)-1,2,3,4-tetrahydronaphthalene hydrochloride | 50 mg |
| Sodium carboxymethyl cellulose | 50 mg |
| S | 1.25 ml |
| Benzoic acid solution | 0.10 ml |
| Flavor | q.v. |
| Color | q.v. |
| Purified water to total | 5 ml |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

FORMULATION 4

An intravenous formulation may be prepared as follows:

|  | Quantity (mg/capsule) |
|---|---|
| 2-Diallylamino-8-(isoxazole-5-yl)-1,2,3,4-tetrahydronaphthalene hydrochloride | 100 mg |
| Isotonic saline | 1000 mg |

The solution of the above ingredients generally is administered intravenously at a rate of 1 ml per minute to a subject suffering from depression.

We claim:

1. A method of treating Irritable Bowel Syndrome in mammals comprising administering to a mammal in need of treatment therefor an effective dose of a compound of formula I

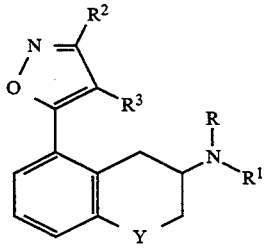

wherein:

R is hydrogen, $C_1$-$C_3$ alkyl, allyl, or

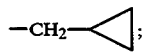;

$R^1$ is hydrogen, $C_1$-$C_3$ alkyl, allyl,

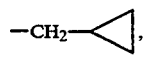, or $(CH_2)_n$—X;

n is 1 to 5;

X is an optionally substituted phenyl, $C_1$-$C_3$ alkoxy, or $C_1$-$C_3$ alkylthio;

$R^2$ and $R^3$ are independently hydrogen, $C_1$-$C_3$ alkyl, $C_1$-$C_3$ alkoxy, $C_1$-$C_3$ alkylthio, halo, CN, phenyl; or together are —$(CH_2)_p$—;

p is 3 to 6;

Y is —$CH_2$—, —O—, —$SO_m$—;

m is 0, 1, or 2;

or a pharmaceutically acceptable acid addition salt or solvate thereof.

2. The method according to claim 1 wherein the mammal is a human.

3. The method according to claim 2 wherein the compound is one in which R is $C_1$-$C_3$ alkyl, or

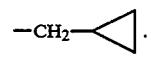.

4. The method according to claim 3 wherein the compound is one in which R is propyl.

5. The method according to claim 4 wherein the compound is one in which $R^1$ is $C_1$-$C_3$ alkyl, or

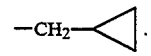.

6. The method according to claim 5 wherein the compound is one in which $R^1$ is propyl.

7. The method according to claim 6 wherein the compound is one in which $R^2$ and $R^3$ are independently hydrogen, $C_1$-$C_3$ alkyl, or together are —$(CH_2)_p$.

8. The method according to claim 6 wherein the compound is one in which $R^2$ and $R^3$ are independently hydrogen or methyl.

9. The method according to claim 7 wherein the compound is one in which $R^2$ and $R^3$ are together —$(CH_2)_p$.

10. The method according to claim 2 wherein the compound is one in which Y is —$CH_2$—.

11. The method according to claim 10 wherein the compound is one in which R is $C_1$-$C_3$ alkyl or

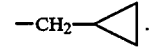.

12. The method according to claim 11 wherein the compound is one in which R is propyl.

13. The method according to claim 10 wherein the compound is one in which $R^1$ is $C_1$-$C_3$ alkyl or

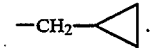.

14. The method according to claim 13 wherein the compound is one in which $R^1$ is propyl.

15. The method according to claim 10 wherein the compound is one in which R and $R^1$ are both propyl.

16. The method according to claim 10 wherein the compound is one in which $R^2$ and $R^3$ are independently hydrogen or $C_1$-$C_3$ alkyl.

17. The method according to claim 10 wherein the compound is one in which $R^2$ and $R^3$ are together —$(CH_2)_p$.

18. The method according to claim 16 wherein the compound is one in which R is $C_1$–$C_3$ alkyl or

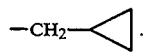

19. The method according to claim 18 wherein the compound is one in which R is propyl.

20. The method according to any of claim 16 wherein the compound is one in which $R^1$ is $C_1$–$C_3$ alkyl or

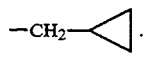

21. The method according to claim 20 wherein the compound is one in which $R^1$ is propyl.

22. The method according to claim 15 wherein the compound is one in which $R^2$ and $R^3$ are independently hydrogen or $C_1$–$C_3$ alkyl.

23. The method according to claim 15 wherein the compound is one in which $R^2$ and $R^3$ are together —$(CH_2)_p$.

24. The method according to claim 2 wherein the compound is one in which Y is —O—.

25. The method according to claim 24 wherein the compound is one in which R is $C_1$–$C_3$ alkyl or

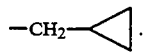

26. The method according to claim 24 wherein the compound is one in which $R^1$ is $C_1$–$C_3$ alkyl or

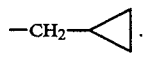

27. The method according to claim 24 wherein the compound is one in which $R^2$ and $R^3$ are independently hydrogen or C1–C3 alkyl.

28. The method according to claim 2 wherein the compound is one in which Y is —SOm—.

29. The method according to claim 28 wherein the compound is one in which R is $C_1$–$C_3$ alkyl or

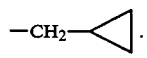

30. The method according to claim 1 wherein the compound is a d-isomer.

31. The method according to claim 30 wherein the compound is one in which $R^1$ is $C_1$–$C_3$ alkyl or

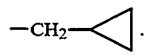

32. The method according to claim 30 wherein the compound is one in which $R^2$ and $R^3$ are independently hydrogen or $C_1$–$C_3$ alkyl.

33. The method according to claim 22 wherein the compound is selected from the group consisting of
8-(isoxazol-5-yl)-2-dipropylamino-1,2,3,4-tetrahydronaphthalene;
8-(4-methylisoxazol-5-yl)-2-dipropylamino-1,2,3,4-tetrahydronaphthalene; and
8-(3-methylisoxazol-5-yl)-2-dipropylamino-1,2,3,4-tetrahydronaphthalene.

34. The method according to claim 1 wherein the compound is an l-isomer.

35. The method according to claim 1 wherein the compound is S-(—)-8-(isoxazol-5-yl)-2-dipropylamino-1,2,3,4-tetrahydronaphthalene or a pharmaceutically acceptable acid addition salt or solvate thereof.

36. The method according to claim 1 wherein the compound is R-(+)-8-(isoxazol-5yl)-2-dipropylamino-1,2,3,4-tetrahydronaphthalene or a pharmaceutically acceptable acid addition salt or solvate thereof.

37. The method according to claim 1 wherein the compound is R-(+)-8-(4-methylisoxazol-5-yl)-2-dipropylamino-1,2,3,4-tetrahydronaphthalene or a pharmaceutically acceptable acid addition salt or solvate thereof.

38. A method for treating Irritable Bowel Syndrome in mammals which comprises administering to a mammal in need of treatment thereof an effective dose of a compound which is both a 5-$HT_{1A}$ agonist and an $M_1$-cholinergic receptor selective agent.

39. A method of claim 38 wherein the compound employed is of the formula

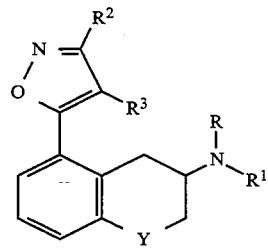

wherein
R is hydrogen, $C_1$–$C_3$ alkyl, allyl, or cyclopropylmethyl;
$R^1$ is hydrogen, $C_1$–$C_3$ alkyl, allyl, cyclopropylmethyl, or $(CH_2)_n$—X;
n is 1 to 5;
X is an optionally substituted phenyl, $C_1$–$C_3$ alkoxy, or $C_1$–$C_3$ alkylthio;
$R^2$ and $R^3$ are independently hydrogen, $C_1$–$C_3$ alkyl, $C_1$–$C_3$ alkoxy, $C_1$–$C_3$ alkylthio, halo, CN, phenyl; or together are —$(CH_2)_p$—;
p is 3 to 6;
Y is —$CH_2$—, —O—, or —$SO_m$—;
m is 0, 1 or 2;
or a pharmaceutically acceptable acid addition salt or solvate thereof.

* * * * *